(12) United States Patent
Gore et al.

(10) Patent No.: US 9,238,002 B2
(45) Date of Patent: *Jan. 19, 2016

(54) SUSPENSIONS OF CYCLOSPORIN A FORM 2

(71) Applicant: ALLERGAN, INC., Irvine, CA (US)

(72) Inventors: Anuradha V. Gore, Irvine, CA (US); Prem Swaroop Mohanty, Irvine, CA (US); E. Quinn Farnes, Laguna Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/325,167

(22) Filed: Jul. 7, 2014

(65) Prior Publication Data

US 2014/0322335 A1 Oct. 30, 2014

Related U.S. Application Data

(62) Division of application No. 13/677,014, filed on Nov. 14, 2012, now Pat. No. 8,796,222.

(60) Provisional application No. 61/559,866, filed on Nov. 15, 2011.

(51) Int. Cl.
| | |
|---|---|
| A61K 38/13 | (2006.01) |
| A61K 9/10 | (2006.01) |
| A61K 9/00 | (2006.01) |
| A61K 47/26 | (2006.01) |
| A61K 47/10 | (2006.01) |
| A61K 47/06 | (2006.01) |
| C07K 7/64 | (2006.01) |

(52) U.S. Cl.
CPC ............. *A61K 9/0048* (2013.01); *A61K 9/0014* (2013.01); *A61K 38/13* (2013.01); *A61K 47/06* (2013.01); *A61K 47/10* (2013.01); *A61K 47/26* (2013.01); *C07K 7/645* (2013.01)

(58) Field of Classification Search
None
See application file for complete search history.

(56) References Cited

U.S. PATENT DOCUMENTS

| | | |
|---|---|---|
| 5,474,979 A | 12/1995 | Ding et al. |
| 6,254,860 B1 | 7/2001 | Garst |
| 6,350,442 B2 | 2/2002 | Garst |
| 7,153,834 B2 | 12/2006 | Patel |
| 2006/0100288 A1 | 5/2006 | Bague et al. |
| 2006/0205639 A1 | 9/2006 | Domb |
| 2008/0009436 A1 | 1/2008 | Chang et al. |

(Continued)

FOREIGN PATENT DOCUMENTS

| | | |
|---|---|---|
| GB | 2211848 | 7/1989 |
| WO | 89-01772 | 3/1989 |
| WO | 2005-072701 | 8/2005 |

(Continued)

OTHER PUBLICATIONS

Declaration Under 37 CFR 1.132 of Prem S. Mohanty for U.S. Appl. No. 13/677,014, filed Oct. 10, 2013.*

(Continued)

*Primary Examiner* — Bethany Barham
*Assistant Examiner* — Dominic Lazaro
(74) *Attorney, Agent, or Firm* — Laura L. Wine; Joel B. German; Debra D. Condino

(57) ABSTRACT

Disclosed herein are methods of formulating cyclosporin A Form 2.

13 Claims, 18 Drawing Sheets

(56) References Cited

U.S. PATENT DOCUMENTS

2008/0299206 A1    12/2008  Lee
2013/0023482 A1    1/2013   Gore et al.

FOREIGN PATENT DOCUMENTS

WO    2009-088570    7/2009
WO    2012-166610    12/2012

OTHER PUBLICATIONS

Bowen, P., Particle Size Distribution Measurement From Millimeters to Nanometers and From Rods to Platelets, Journal of Dispersion Science and Technology, 2002, 631-662, 23(5).

Cedarstaff, Thomas et al, A Comparative Study of Tear Evaporation Rates and Water Content of Soft Contact Lenses, American Journal of Optometry & Physiological Optics, 1983, 167-174, 60(3).

Lechuga-Ballesteros, David et al, Properties and Stability of a Liquid Crystal Form of Cyclosporine—The First Reported Naturally occurring Peptide That Exists as a Thermotropic Liquid Crystal, Journal of Pharmaceutical Sciences, Sep. 2003, 1821-1831, 92(9).

Patent Cooperation Treaty, Notification of Transmittal of the International Search Report and the Written Opinion of the International Searching Authority, or the Declaration, Form PCT/ISA/220, Int. App. No. PCT/US2012/065011, Jan. 25, 2013.

Zhou, Yunlong, Cyclosporin A: Solubilization, Solid Dispersion and Solid-State Transformation, A Thesis Submitted to the Faculty of Purdue University, 157 Pages. 2000.

\* cited by examiner

| Formulation | Mean Values | | | |
|---|---|---|---|---|
| | $C_{max}$ (ng/g) | $AUC_{0-24}$ (ng·hr/g) | Relative %F | $T_{max}$ (hr) |
| A | 369 ± 64 | 5940 ± 467 | 98 | 24 |
| A1 | 217 ± 57 | 3900 ± 309 | 64 | 6 |
| B1 | 358 ± 96 | 6230 ± 761 | 515 | 6 |
| D | 205 ± 58 | 3940 ± 428 | 65 | 24 |
| Restasis | 296 ± 65 | 6050 ± 574 | 100 | 12 |

FIG. 6

|   | Conjunctiva Bulbar | | | | Conjunctiva Palpebral | | | |
|---|---|---|---|---|---|---|---|---|
|   | $C_{max}$ (ng/g) | $AUC_{0-24}$ (ng·hr/g) | Relative %F | $T_{max}$ (hr) | $C_{max}$ (ng/g) | $AUC_{0-24}$ (ng·hr/g) | Relative %F | $T_{max}$ (hr) |
| A | 240 ± 120 | 1580 ± 136 | 100 | 0.5 | 553 ± 132 | 3280 ± 288 | 100 | 0.5 |
| B1 | 261 ± 80 | 1530 ± 117 | 484 | 0.5 | 687 ± 142 | 4250 ± 359 | 648 | 0.5 |

FIG. 9

| Formulation | Accessory Lacrimal Gland | | |
|---|---|---|---|
| | $C_{max}$ (ng/g) | $AUC_{0-24}$ (ng·hr/g) | $T_{max}$ (hr) |
| A | 1.77 ± 1.66 | 8.40 ± 2.54 | 0.5 |
| B1 | 0.502 ± 0.588 | NC | 0.5 |

FIG. 13

SUSPENSIONS OF CYCLOSPORIN A FORM 2

CROSS-REFERENCE TO RELATED APPLICATION

This patent application is a divisional of copending U.S. patent application Ser. No. 13/677,014, filed Nov. 14, 2012, which claims priority to U.S. Provisional Patent Application No. 61/559,866, filed Nov. 15, 2011, the entire contents of which are hereby incorporated by reference.

FIELD OF THE INVENTION

This invention relates to the fields of nanotechnology and drug formulation technology.

BACKGROUND

Cyclosporine A is the active ingredient in Restasis®, a drug that is used to treat dry eye disease. Cyclosporin A is poorly soluble in water, and so is currently formulated either by dissolving the drug in oil to form an emulsion, or by mixing the drug with high levels of surfactants and/or solubilizers to form an aqueous solution. The inventors have discovered a formulation of cyclosporin A using a new crystalline polymorph of cyclosporin A, to create nanosuspensions comprising particles of cyclosporin A having an average size of around 1 micrometer or less (to put that number in perspective, the average thickness of a human hair is around 100 micrometers).

A nanosuspension of cyclosporin A, when delivered topically to the eye, may have one or more advantages, including the following:

a higher bioavailability compared to suspensions, due to the higher surface area available for dissolution;

a longer retention on the eye due to smaller particles, leading to further improvement in bioavailability;

a lower potential for foreign body sensation or particle irritation, thus reducing tearing and drainage of formulations from the eye;

a lower level of surfactants or solubilizers in the formulation, improving tolerability and bioavailability of the drug.

BRIEF DESCRIPTION OF THE FIGURES

FIGS. 5-13 show the results when four different formulations according to the invention (summarized in Table 2) and Restasis® are administered to NZW female rabbits (two rabbits total, one formulation per eye) in a single topical dose:

FIG. 5 shows concentrations in the cornea.
FIG. 6 summarizes pharmacokinetic data.
FIG. 7 shows concentrations in the bulbar conjunctiva.
FIG. 8 shows concentrations in the palpebral conjunctiva.
FIG. 9 summarizes pharmacokinetic data for the bulbar conjunctiva and palpebral conjunctiva.
FIG. 10 shows concentrations in the bulbar conjunctiva.
FIG. 11 shows concentrations in the palpebral conjunctiva.
FIG. 12 shows concentrations in the lacrimal gland.
FIG. 13 summarizes pharmacokinetic data for lacrimal gland.

DETAILED DESCRIPTION

Cyclosporin A

Cyclosporin A (CsA) is a cyclic peptide having the following chemical structure:

Its chemical name is cyclo[[(E)-(2S,3R,4R)-3-hydroxy-4-methyl-2-(methylamino)-6-octenoyl]-L-2-aminobutyryl-N-methylglycyl-N-methyl-Lleucyl-L-valyl-N-methyl-L-leucyl-L-alanyl-D-alanyl-N-methyl-L-leucyl-N-methyl-L-leucyl-Nmethyl-L-valyl]. It is also known by the names cyclosporine, cyclosporine A, ciclosporin, and ciclosporin A. It is the active ingredient in Restasis® (Allergan, Inc., Irvine, Calif.), an emulsion comprising 0.05% (w/v) cyclosporin. Restasis® is approved in the United States to increase tear production in patients whose tear production is presumed to be suppressed due to ocular inflammation associated with keratoconjunctivitis sicca.

Cyclosporin A Form 2

Cyclosporin A is known to exist in an amorphous form, liquid crystal form, tetragonal crystalline form (form 1), and an orthorhombic form (form 3). A new crystalline form, cyclosporin A Form 2, has recently been discovered.

Figure 14:
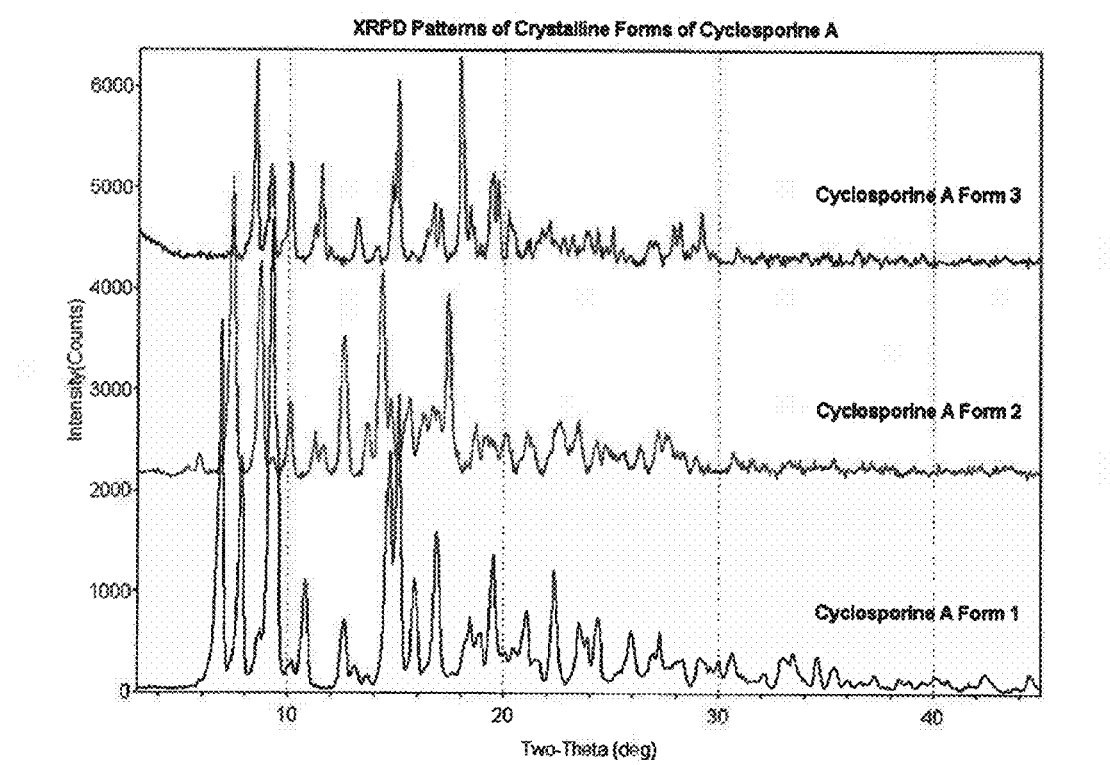
FIG. 14 depicts characteristic X-ray powder diffraction (XRPD) patterns of CsA in a new crystalline form (designated as Form 2 herein), tetragonal form (designated as Form 1 herein), and orthorhombic form (designated as Form 3 herein).
Figure 15:
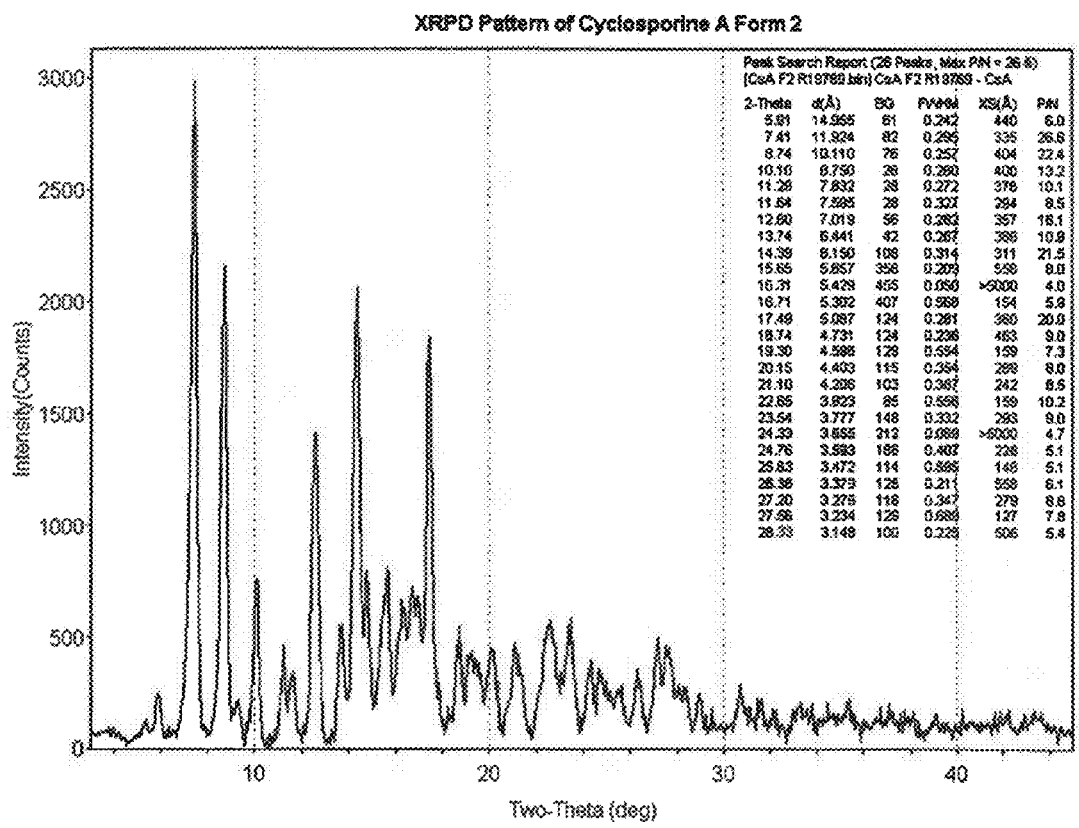
FIG. 15 depicts the XRPD diffractogram of CsA crystalline Form 2.

The XRPD pattern of CsA Form 2 differs significantly from the tetragonal form and orthorhombic form (FIG. 14). The major crystalline peaks for CsA form 2 appear at (2θ) when scanned by an X-ray diffractometer with X-ray source as Cu Kα radiation, λ=1.54 Å, at 30 kV/15 mA: 7.5, 8.8, 10.2, 11.3, 12.7, 13.8, 14.5, 15.6 and 17.5 (d-spacing in crystal lattice at about 11.8, 10.0, 8.7, 7.8, 7.0, 6.4, 6.1, 5.6 and 5.1 Å, respectively, FIG. 15). These major peaks are defined as those being unique to Form 2 relative to the orthorhombic or tetragonal forms; as well as, peaks having an intensity greater than 5 times the background.

In one embodiment, the new crystalline form (Form 2) of CsA is a nonstoichiometric hydrate of Cyclosporin A. In another embodiment, the crystalline Form 2 is represented by the formula:

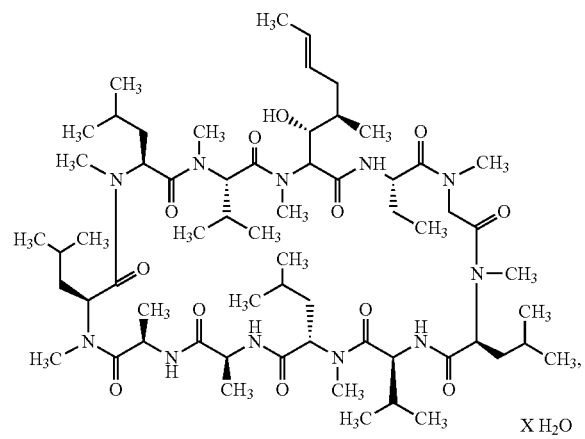

wherein X is the number of molecules of water and varies from 0 to 3. In one embodiment, X in the above formula is 2.

Form 2 appears to be a kinetically stable form of CsA in aqueous suspensions. Suspensions containing Form 2 show no conversion to other known polymorphic or pseudomorphic forms upon storage. It has been found that Form 1 and the amorphous form convert to Form 2 in the presence of water.

The single crystal structure of the hydrate form of CsA Form 2 has been determined and the crystal structure parameters are listed in Table 2. These results indicate that Form 2 is unique compared to other known crystalline forms of cyclosporine A.

TABLE 1

Crystal data and data collection parameters of crystal structure solution of CsA Form 2.

| formula | $C_{62}H_{115}N_{11}O_{14}$ |
|---|---|
| formula weight | 1238.67 |
| space group | $P\,2_1\,2_1\,2_1$ (No. 19) |
| a (Å) | 12.6390(5) |
| b (Å) | 19.7582(8) |
| c (Å) | 29.568(2) |
| volume (Å³) | 7383.8(7) |
| Z | 4 |
| $d_{calc}$ (g cm⁻³) | 1.114 |
| crystal dimensions (mm) | 0.27 × 0.18 × 0.12 |
| temperature (K) | 150 |
| radiation (wavelength in Å) | Cu $K_\alpha$ (1.54184) |
| monochromator | confocal optics |
| linear abs coef (mm⁻³) | 0.640 |
| absorption correction applied | empirical[a] |
| transmission factors (min, max) | 0.80, 0.93 |
| diffractometer | Rigaku RAPID-II |
| h, k, l range | −13 to 13 −21 to 21 −32 to 21 |
| 2θ range (deg) | 5.38-115.00 |
| mosaicity (deg) | 1.31 |
| programs used | SHELXTL |
| $F_{000}$ | 2704.0 |

TABLE 1-continued

Crystal data and data collection parameters of crystal structure solution of CsA Form 2.

| weighting | $1/[\sigma^2(Fo^2) + (0.0845P)^2 + 0.0000P]$ where P = $(Fo^2 + 2Fo^2)/3$ |
|---|---|
| data collected | 37360 |
| unique data | 9964 |
| $R_{int}$ | 0.077 |
| data used in refinement | 9964 |
| cutoff used in R-factor calculations | $F_o^2 > 2.0s(F_o^2)$ |
| data with I > 2.0s(I) | 6597 |
| number of variables | 834 |
| largest shift/esd in final cycle | 0.00 |
| $R(F_o)$ | 0.061 |
| $R_w(F_o^2)$ | 0.145 |
| goodness of fit | 1.037 |
| absolute structure determination | Flack parameter[b] (0.0(3)) |

Figure 8:
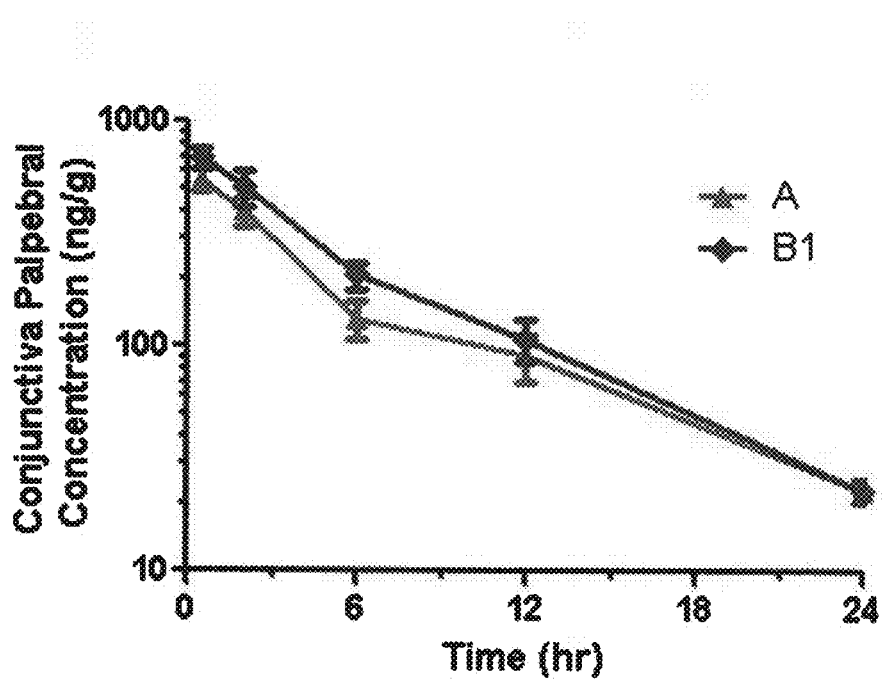
Figure 10:
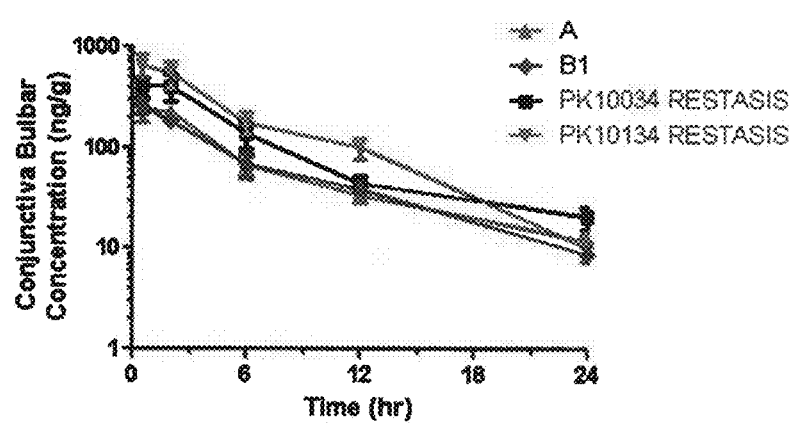
Figure 11:
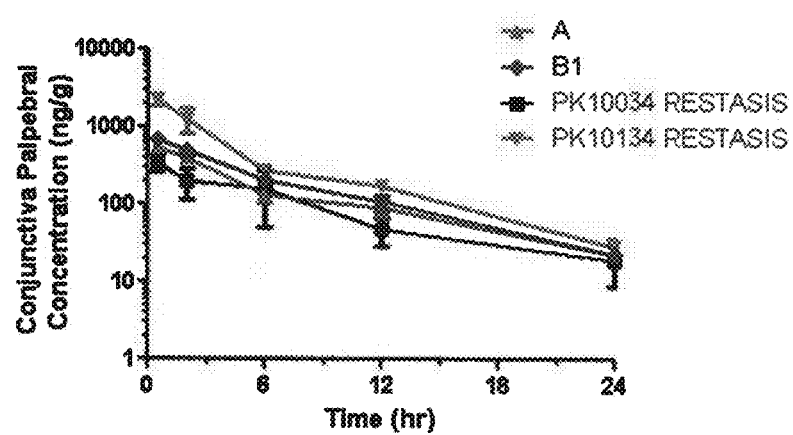
Figure 12:
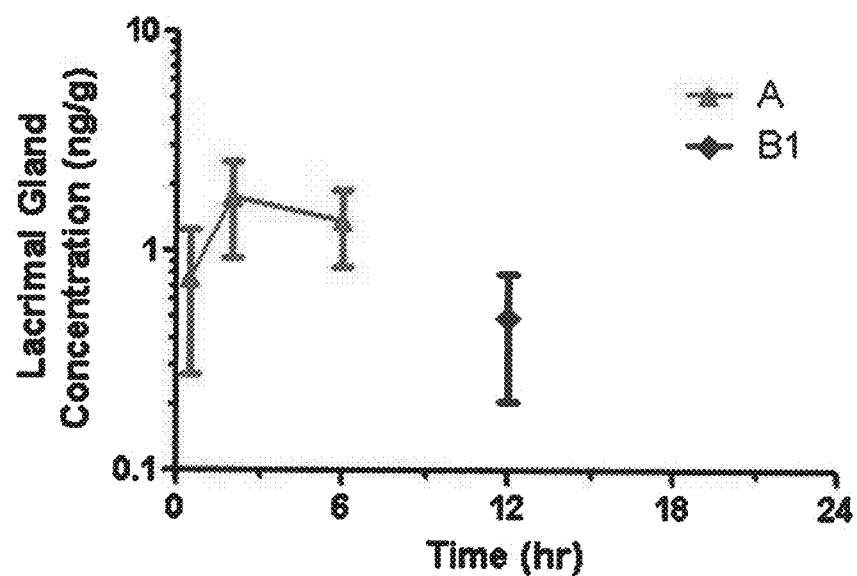

The asymmetric unit of this CsA Form 2 contains one cyclosporine A molecule and two water molecules. It is possible that any small molecule that can hydrogen bond to water could play the role of space filler, which would give a range of potential structures running from the orthorhombic dihydrate to distorted monoclinic dihydrate The XRPD pattern calculated from the single-crystal structure is shown in FIG. 8 and it matches the experimental pattern shown in FIG. 2. These matching patterns further corroborate that Form 2 is a unique and pure crystalline form of cyclosporine A.

Figure 16:
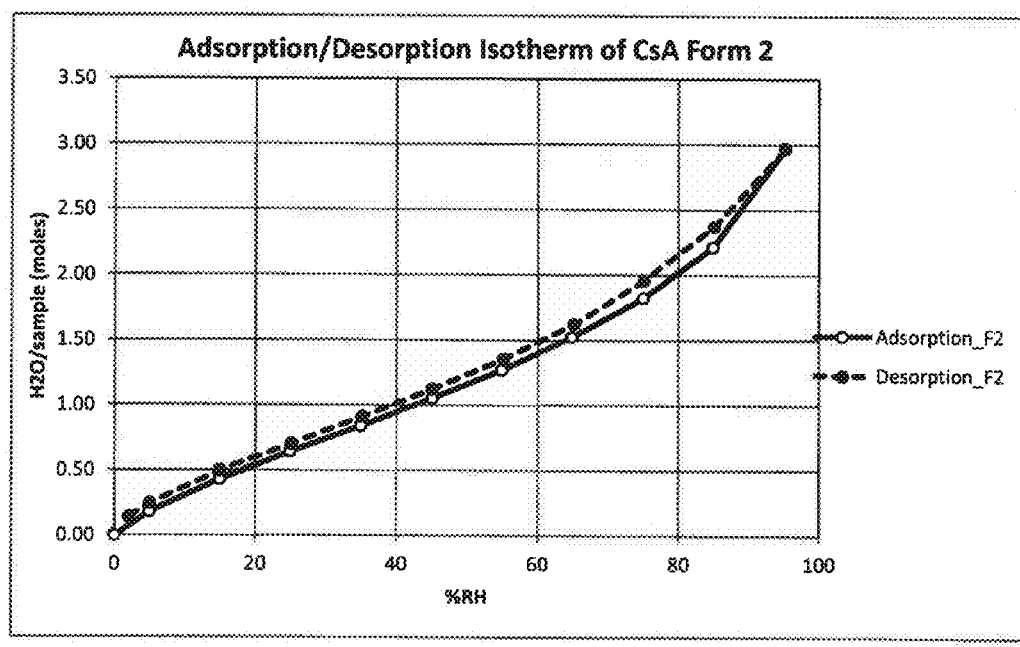
FIG. 16 depicts the water sorption/desorption profile of CsA Form 2.
Figure 17:
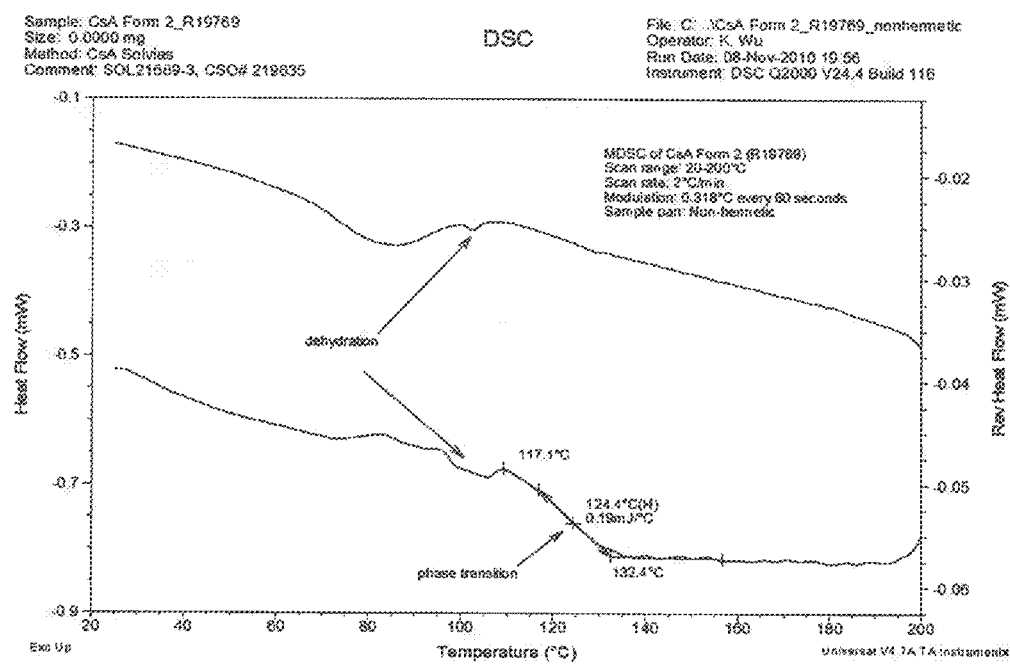
FIG. 17 depicts MDSC analysis of CsA Form 2 recovered from 0.04% formulation with 1% PS80.
Figure 18:
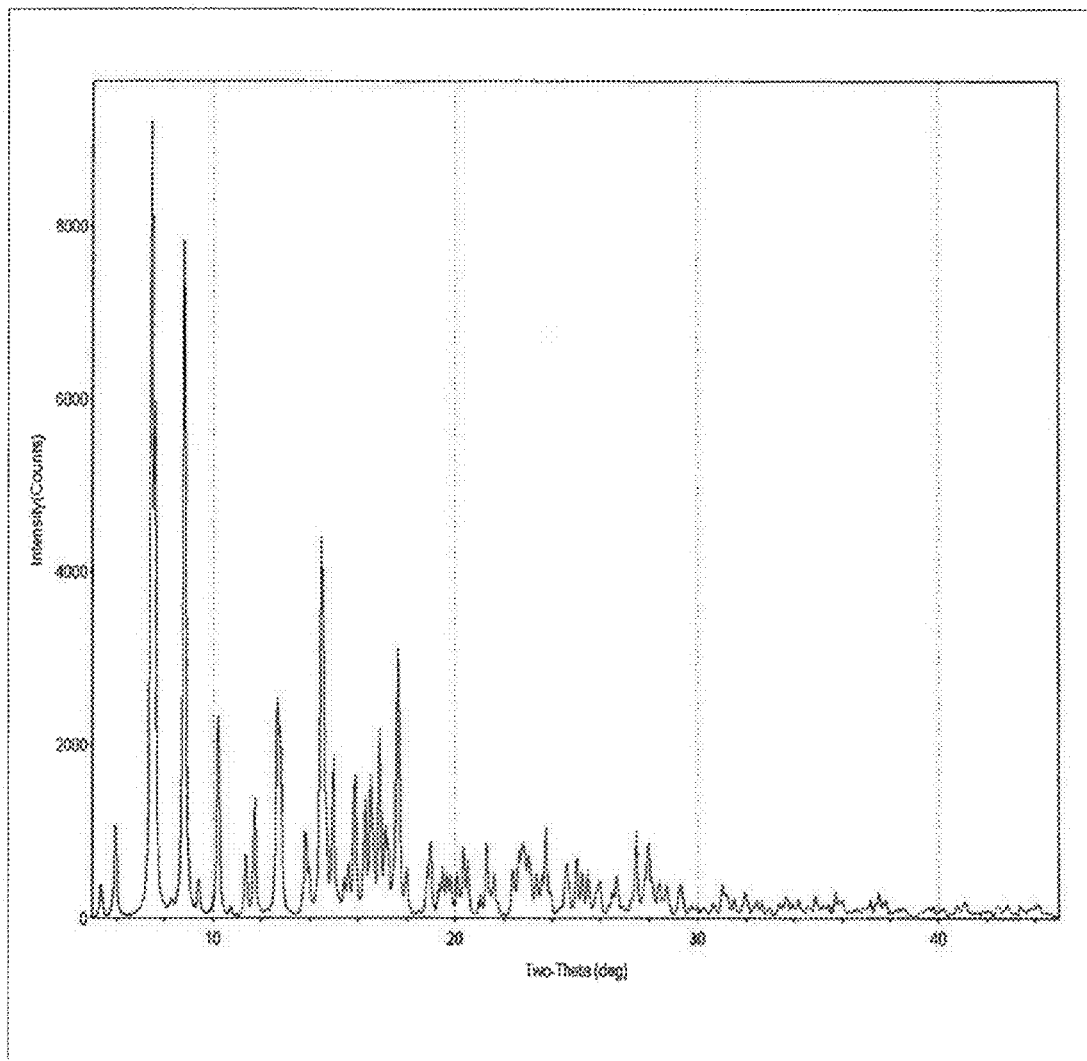
FIG. 18 shows the simulated XRPD pattern of cyclosporine A forms.

Without wishing to be bound by theory, thermogravimetric analysis combined with KF titration and vapor sorption desorption analysis (VSA) suggest that CsA Form 2 is a nonstoichiometric hydrate of CsA. The vapor sorption analysis of Cyclosporine Form 2 indicates that water content in the new crystal form reversibly varies with relative humidity as shown in FIG. 16. Similar to the tetragonal form, the new CsA form undergoes a phase transition to a liquid crystal or amorphous form at 124.4° C. prior to melting as indicated by the modulated differential calorimetric (MDSC) analysis (FIG. 17).

Cyclosporin A Form 2 may be obtained by suspending amorphous 0.05% cyclosporin A (w/v) in 1% Polysorbate 80, heating the solution to 65° C., holding it at that temperature for 24 hours, and then recovering the precipitate by vacuum filtration. One can then use the cyclosporin A Form 2 thus obtained to generate additional amounts, using Cyclosporin A Form 2 as a seed crystal; in this method, one suspends about 30 g cyclosporin A in a solution of 900 ml water containing 1% (w/v) Polysorbate 80, heats the solution to 65° C., and then seeds it with 0.2 g of cyclosporin A Form 2 at a temperature of 52° C. The solution is then stirred for about 22 hours at a temperature of between about 61° C. and 65° C., and then recovers the precipitate that results.

Further details regarding CsA Form 2 may be found in U.S. patent application Ser. No. 13/480,710, the entire contents of which are incorporated by reference herein.

Suspensions of Cyclosporin A Form 2

Compositions of the invention are ophthalmically acceptable suspensions of Cyclosporin A form 2. By "ophthalmically acceptable," the inventors mean that the suspensions are formulated in such a way as to be non-irritating when administered to the eye of a mammal, such as a human. In one embodiment, the compositions are suspensions; that is, they comprise particles of cyclosporin A form 2, having an average particle size greater than about 1 µm, dispersed throughout a liquid vehicle. In another embodiment, the compositions are nanosuspensions; that is, they comprise particles of cyclosporin A form 2, having an average particle size of less than about 1 µm, that are dispersed throughout a liquid vehicle.

In one embodiment, the suspension comprises cyclosporin A form 2 at a concentration of about 0.001% to about 10% (w/v). In one embodiment, the suspension comprises cyclosporin A form 2 at a concentration of about 0.001% (w/v) to about 0.01%, about 0.001% (w/v) to about 0.04% (w/v), about 0.001% (w/v) to about 0.03% (w/v), about 0.001% (w/v) to about 0.02% (w/v), or about 0.001% (w/v) to about 0.01% (w/v). In another embodiment, the suspension comprises cyclosporin A form 2 at a concentration of about 0.01% (w/v) to about 0.05%, about 0.01% (w/v) to about 0.04% (w/v), about 0.01% (w/v) to about 0.03% (w/v), about 0.01% (w/v) to about 0.02% (w/v), or about 0.01% (w/v) to about 0.01% (w/v). In another embodiment, the suspension comprises cyclosporin A form 2 at a concentration of about 0.01% (w/v) to about 0.1%, about 0.1% (w/v) to about 0.5% (w/v), about 0.01% (w/v) to about 1% (w/v), or about 1% (w/v) to about 10%.

For example, the suspensions may comprise about 0.001% (w/v), about 0.002% (w/v), about 0.003% (w/v), about 0.004% (w/v), about 0.005% (w/v), about 0.006% (w/v), about 0.007% (w/v), about 0.008% (w/v), about 0.009% (w/v), about 0.01% (w/v), about 0.015% (w/v), about 0.02% (w/v), about 0.025% (w/v), about 0.03% (w/v), about 0.035% (w/v), about 0.04% (w/v), about 0.045% (w/v), about 0.05% (w/v), about 0.055% (w/v), about 0.06% (w/v), about 0.065% (w/v), about 0.07% (w/v), about 0.075% (w/v), about 0.08% (w/v), about 0.085% (w/v), about 0.09% (w/v), about 0.095% (w/v), about 0.1% (w/v), about 0.15% (w/v), about 0.2% (w/v), about 0.25% (w/v), about 0.3% (w/v), about 0.35% (w/v), about 0.4% (w/v), about 0.45% (w/v), about 0.5% (w/v), about 0.55% (w/v), about 0.6% (w/v), about 0.65% (w/v), about 0.7% (w/v), about 0.75% (w/v), about 0.8% (w/v), about 0.85% (w/v), about 0.9% (w/v), about 0.95% (w/v), or about 1.0% (w/v) cyclosporin A form 2.

In one embodiment, the suspension comprises a surfactant. In one embodiment, the surfactant is selected from polyoxyethylene (20) sorbitan monooleate (Polysorbate 80), polyethylene glycol 660 hydroxystearate (Solutol), polyoxyethylene (40) stearate Myrj 52 (POE-40-Stearate), pluronic F68 (Polaxamer 188), polyoxyethylene sorbitan monolaurate (Polysorbate 20), and sodium glycocholate (NaGC). The vehicle may contain all of these surfactants, or one, two, three, four, or five of them.

One can use between about 0.001% (w/v) and about 5% (w/v) of the surfactant. In one embodiment, the suspensions contain about 0.001% (w/v) to about 1% (w/v), about 0.001% (w/v) to about 0.1% (w/v), about 0.01% (w/v) to about 0.1% (w/v), or about 0.1% (w/v) to about 1% (w/v) of the surfactant. For example, the suspensions may contain about 0.001% (w/v), about 0.002% (w/v), about 0.003% (w/v), about 0.004% (w/v), about 0.005% (w/v), about 0.006% (w/v), about 0.007% (w/v), about 0.008% (w/v), about 0.009% (w/v), about 0.01% (w/v), about 0.02% (w/v), about 0.03% (w/v), about 0.04% (w/v), about 0.05% (w/v), about 0.06% (w/v), about 0.07% (w/v), about 0.08% (w/v), about 0.09% (w/v), about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1% (w/v), about 2% (w/v), about 3% (w/v), about 4% (w/v), or about 5% (w/v) of the surfactant.

When using more than one surfactant, the suspension may contain the same or different amounts of each.

In addition to a surfactant, the suspensions may comprise a stabilizer. In one embodiment, the stabilizer is selected from hydroxy propyl cellulose, hydroxypropylmethyl cellulose, hydroxyethylcellulose, polyvinyl pyrolidone, carboxymethylcellulose, Pemulen®, and Pemulen® TR-2. Pemulen® is the trade name for high molecular weight, crosslinked copolymers of acrylic acid and C10-C30 alkyl acrylate produced by Lubrizol Corp. Pemulen® TR-2 is a C10-30 alkyl acrylate crosspolymer containing a higher level of hydrophobic groups than other Pemulen® polymers. The vehicle may contain all of these stabilizers, or none of them, or it may contain one, two, three, four, or five of them.

One can use between about 0.01% (w/v) and about 10% (w/v) of the stablizer. In one embodiment, the suspensions contain about 0.01% (w/v) to about 1% (w/v), or about 0.01% (w/v) to about 0.1% (w/v), or about 0.1% (w/v) to about 1% (w/v) of the stabilizer. For example, the suspensions may contain about about 0.01% (w/v), about 0.02% (w/v), about 0.03% (w/v), about 0.04% (w/v), about 0.05% (w/v), about 0.06% (w/v), about 0.07% (w/v), about 0.08% (w/v), about 0.09% (w/v), about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1% (w/v), about 2% (w/v), about 3% (w/v), about 4% (w/v), about 5% (w/v), about 6% (w/v), about 7% (w/v), about 8% (w/v), about 9% (w/v), or about 10% of the stablizer.

When using more than one surfactant, the suspension may contain the same or different amounts of each.

In addition to a surfactant, the vehicle may also comprise a tonicity adjustor selected from glycerin, mannitol, sodium citrate dihydrate, potassium chloride, boric acid, and sodium borate decahydrate. The tonicity adjustor is added as needed to achieve the desired tonicity; the vehicle may contain all of these tonicity adjusters, or none of them, or it may contain one, two, three, four, or five of them. In one embodiment, the tonicity adjustors are present in an amount of between about 0.1% (w/v) and about 10% (w/v). When using more than one tonicity adjustor, the suspension may contain the same or different amounts of each.

The suspension usually contains water, in an amount sufficient to provide a desired pH, tonicity, and other characteristics that would make the suspension appropriate for administration to the eye.

Methods of Preparing Suspension of Cyclosporin A Form 2

The formulations of the invention may be made by mixing cyclosporin A form 2 with the appropriate surfactants, stabilizers, and tonicity adjustors, as described above, to form a suspension If fine particles of cyclosporin A are desired, the suspension is then milled using a high pressure homogenizer, such as those commercially available from Microfluidics Intl Corp. of Newton, Mass. A unique and surprising property of cyclosporin form A 2 is that it may be milled, if desired, to obtain a suspension with an average particle size (d90) of less than 1 μm. The cyclosporin A in such a nanosuspension has higher bioavailability compared to other (macro) suspensions of cyclosporin A, due to the higher surface area available for dissolution; bioavailability is further enhanced because the smaller particles enable the Cyclosporin A to be retained on the eye longer. The smaller particles of the nanosuspensions result in a formulation with a lower potential to produce a foreign body sensation or other irritation that a subject perceives when the formulation is instilled in the eye. Also, because the particles are smaller, they associate more readily with surfactants and stabilizers, thereby permitting one to use lower concentrations of them.

After the cyclosporin A form 2 suspension is milled, it is diluted to obtain the final product.

Methods of Treatment

Compositions of the invention may be used to treat any condition of the eye which is known to be amenable to topical treatment with cyclosporin A (such as with Restasis®) at the concentrations stated here. For example, compositions of the invention may be used to treat patients suffering from dry eye, to treat blepharitis and meibomian gland disease, to restore corneal sensitivity that has been impaired due to refractive surgery on the eye, to treat allergic conjunctivitis and atopic and vernal keratoconjunctivitis, and to treat ptyregia, conjunctival and corneal inflammation, keratoconjuntivitis, graft versus host disease, post-transplant glaucoma, corneal transplants, mycotic keratitis, Thygeson's superficial punctate keratitis, uveitis, and Theodore's superior limbic keratoconjunctivitis, among other conditions.

The International Dry Eye Workshop (DEWS) defines dry eye as "a multifactorial disease of the tears and ocular surface that results in symptoms of discomfort, visual disturbance, and tear film instability with potential damage to the ocular surface, accompanied by increased osmolarity of the tear film and inflammation of the ocular surface." It includes those conditions, such as keratoconjunctivitis sicca, that are caused by tear deficiency or excessive evaporation of tears.

Blepharitis is a chronic disorder producing inflammation of the anterior and posterior lid margin, with involvement of skin and its related structures (hairs and sebaceous glands), the mucocutaneous junction, and the meibomian glands. It can also affect the conjunctiva, tear film, and the corneal surface in advanced stages and may be associated with dry eye. Blepharitis is commonly classified into anterior or posterior blepharitis, with anterior affecting the lash bearing region of the lids, and posterior primarily affecting the meibomian gland orifices.

Meibomian gland disease most often occurs as one of three forms: primary meibomitis, secondary meibomitis, and meibomian seborrhea. Meibomian seborrhea is characterized by excessive meibomian secretion in the absence of inflammation (hypersecretory meibomian gland disease). Primary meibomitis, by contrast, is distinguished by stagnant and inspissated meibomian secretions (obstructive hypersecretory meibomian gland disease). Secondary meibomitis represents a localized inflammatory response in which the meibomian glands are secondarily inflamed in a spotty fashion from an anterior lid margin blepharitis.

Impaired corneal sensitivity often occurs after refractive surgery, such as photorefractive keratectomy, laser assisted sub-epithelium keratomileusis (LASEK), EPI-LASEK, customized transepithelial non-contact ablation, or other procedures in which the corneal nerves are severed. Impaired corneal sensitivity may also occur after viral infection, such as by HSV-1, HSV-2, and VZV viruses. Patients with impaired corneal sensitivity often complain that their eyes feel dry, even though tear production and evaporation may be normal, suggesting that "dryness" in such patients is actually a form of corneal neuropathy that results when corneal nerves are severed by surgery or inflamed after viral infection.

Allergic conjunctivitis is an inflammation of the conjunctiva resulting from hypersensitivity to one or more allergens. It may be acute, intermittent, or chronic. It occurs seasonally, that is, at only certain time of the year, or it occurs perennially, that is, chronically throughout the year. Symptoms of seasonal and perennial allergic conjunctivitis include, in addition to inflammation of the conjunctiva, lacrimation, tearing, conjunctival vascular dilation, itching, papillary hyperlasia, chemosis, eyelid edema, and discharge from the eye. The discharge may form a crust over the eyes after a night's sleep.

Atopic keratoconjunctivitis is a chronic, severe form of allergic conjunctivitis that often leads to visual impairment. Symptoms include itching, burning, pain, redness, foreign body sensation, light sensitivity and blurry vision. There is often a discharge, especially on awakening from a night's sleep; the discharge may be stringy, ropy, and mucoid. The lower conjunctiva is often more prominently affected than the upper conjunctiva. The conjunctiva may range from pale, edematous, and featureless to having the characteristics of advanced disease, including papillary hypertrophy, subepithelial fibrosis, formix foreshortening, trichiasis, entropion, and madurosis. In some patients the disease progresses to punctate epithelial erosions, corneal neovascularization, and other features of keratopathy which may impair vision. There is typically goblet cell proliferation in the conjunctiva, epithelial pseudotubular formation, and an increased number of degranulating eosinophils and mast cells in the epithelium. CD25+T lymphocytes, macrophages, and dendritic cells (HLA.DR.sup.+, HLA-CD1+) are significantly elevated in the substantia propria.

Like atopic keratoconjunctivitis, vernal keratoconjunctivitis is a severe form of allergic conjunctivitis, but it tends to affect the upper conjunctiva more prominently than the lower. It occurs in two forms. In the palpebral form, square, hard, flattened, closely packed papillae are present; in the bulbar (limbal) form, the circumcorneal conjunctiva becomes hypertrophied and grayish. Both forms are often accompanied by a mucoid discharge. Corneal epithelium loss may occur, accompanied by pain and photophobia, as may central corneal plaques and Trantas' dots.

EXAMPLES

The invention is further illustrated by the following examples.

Example 1

The inventors prepared the following compositions:

TABLE 1

| Formulations of cyclosporin A prepared in Example 1 | | | | | | |
|---|---|---|---|---|---|---|
| Ingredient | A | B | C | D | E | F |
| | Concentration % (w/v) | | | | | |
| CsA | | | 0.01 to 0.05 | | | |
| Polysorbate 80 | | | 0.001 to 0.05 | | | |
| Glycerin | 1 | 1.2 | 1.2 | 1 | 1.2 | 2.2 |
| Mannitol | 0.5 | | | | | |
| CMC | 0.5 | | | | | |
| HEC | | 0.1-0.5 | | | | |
| Pemulen TR-2 | | | 0.01-0.1 | | | 0.05-0.1 |
| HPMC | | | | 0.1-1.0 | | |
| PVP | | | | | 0.1-10.0 | |
| Sodium Citrate Dihydrate | 0.4 | 0.4 | 0.4 | 0.4 | 0.4 | |
| Potassium Chloride | 0.14 | | | | | |
| Boric Acid | 0.25 | 0.25 | 0.25 | 0.25 | 0.25 | |
| Sodium Borate Decahydrate | 0.41 | 0.41 | 0.41 | 0.41 | 0.41 | |
| Purified Water | qs | Qs | qs | qs | qs | Qs |

The formulations of Table 1 were prepared by the following process:

1. Preparation of Concentrated Cyclosporin a Nanosuspensions
   a. Cyclosporin A was mixed with an appropriate vehicle to form a suspension. The concentration of Cyclosporin A in this suspension is in the range of 1-10%.
   b. The cyclosporin A suspension was milled using a high pressure homogenizer (a Microfluidizer®, manufactured by Microfluidics, Newton, Mass.) or a ball mill to get nanosuspensions such that d90<11 Jm.

c. Vehicles used for preparation of nanosuspension concentrate are as listed in Table 1
2. Preparation of Final Product
a. The concentrated nanosuspensions prepared in Step-1 were diluted in vehicles suitable for ophthalmic dosing to obtain final product at required dose strength of cyclosporin A. Vehicles suitable for dilution may contain buffers, stabilizers, gelling agents and/or dilution to obtain final formulations with desired concentration of CsA.
b. Compositions of nanosuspension formulations prepared after dilution of the nanosuspension concentrates are listed in Table 2, Particle-size distribution of the different Formulations are shown in FIGS. 1, 2, and 3.

Figure 1:
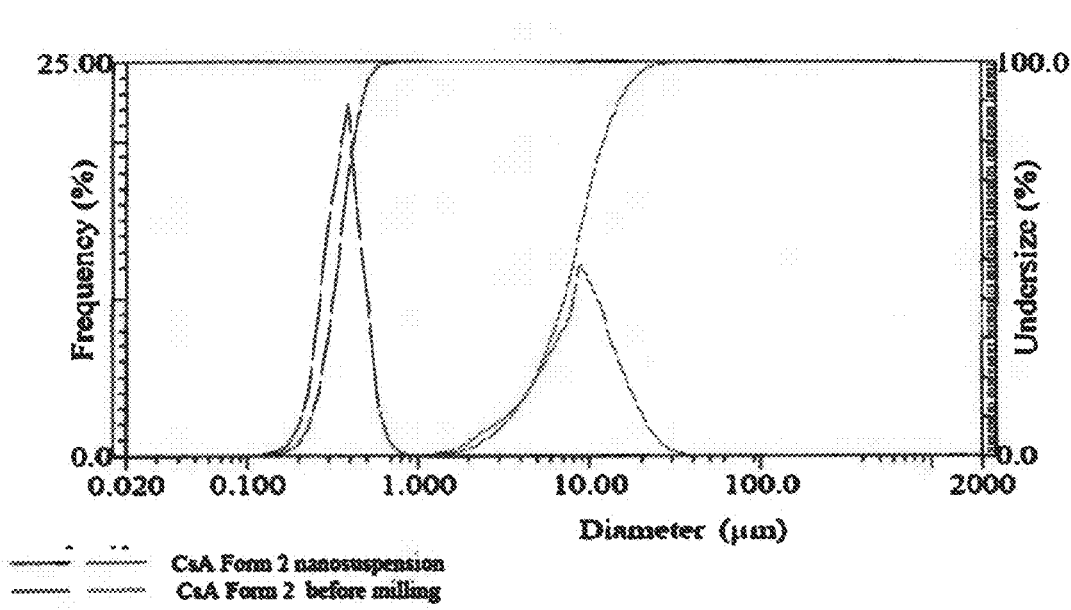
FIG. 1 shows the particle size distribution of cyclosporin A Form 2 nanosuspensions prepared using a high pressure homogenizer compared to suspensions prior to milling.

FIG. 1 shows the particle size distribution of cyclosporin A Form 2 nanosuspensions prepared using a high pressure homogenizer compared to suspensions prior to milling.

Figure 2:
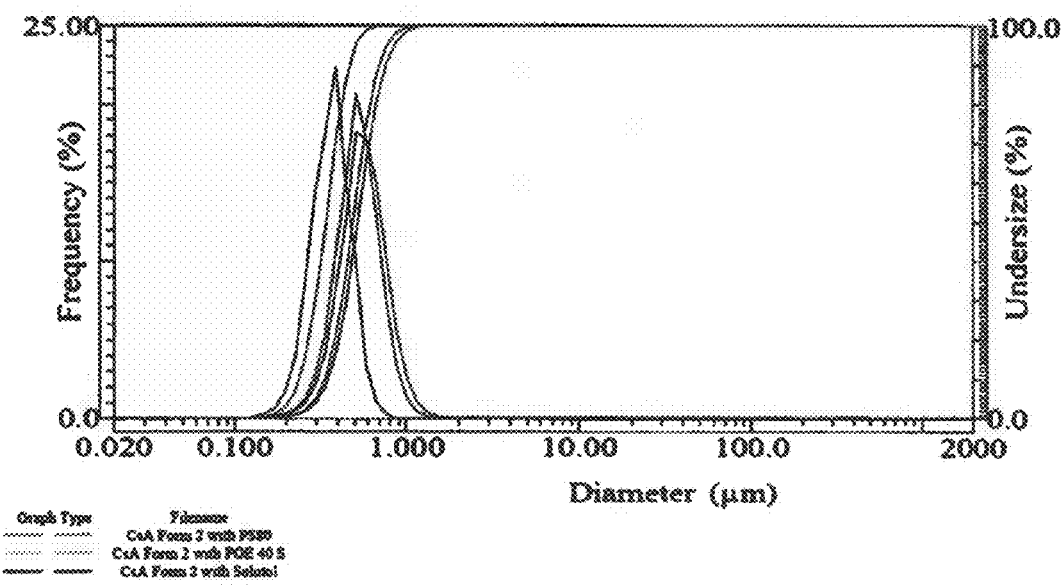
FIG. 2 compares the particle size distribution of cyclosporin A Form 2 nanosuspensions prepared using different surfactants and stabilizers.

FIG. 2 compares the particle size distribution of cyclosporin A Form 2 nanosuspensions prepared using different surfactants and stabilizers.

Figure 3:
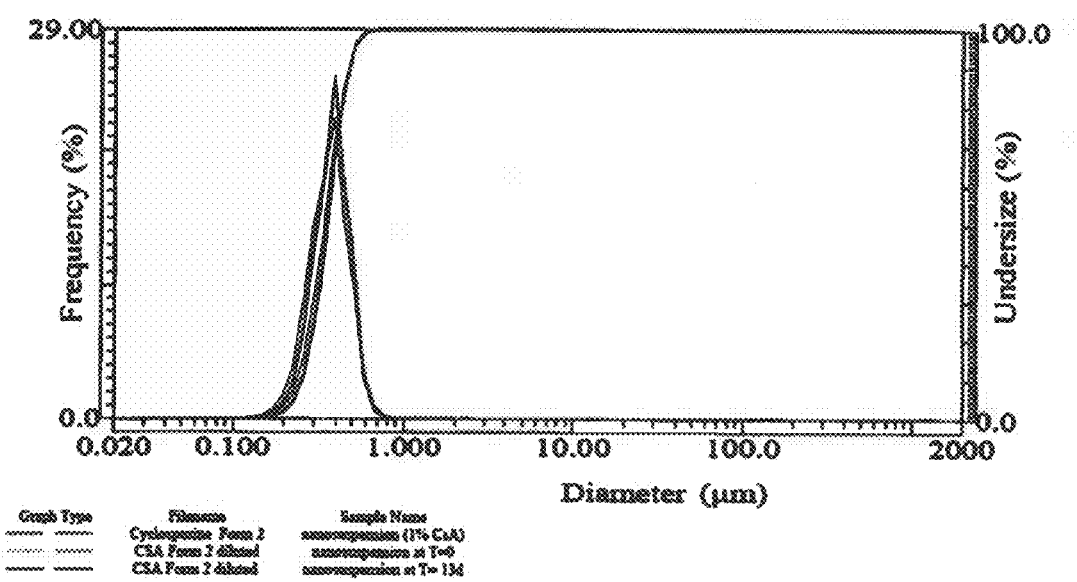
FIG. 3 shows the particle size distribution of Formulation diluted in vehicle containing Na CMC.

FIG. 3 shows the particle size distribution of Formulation diluted in vehicle containing Na CMC (Table-2, vehicle A). Note that no change in particle size is seen in the diluted Formulations over 2 weeks as compared to the nanosuspension concentrate.

Figure 4:
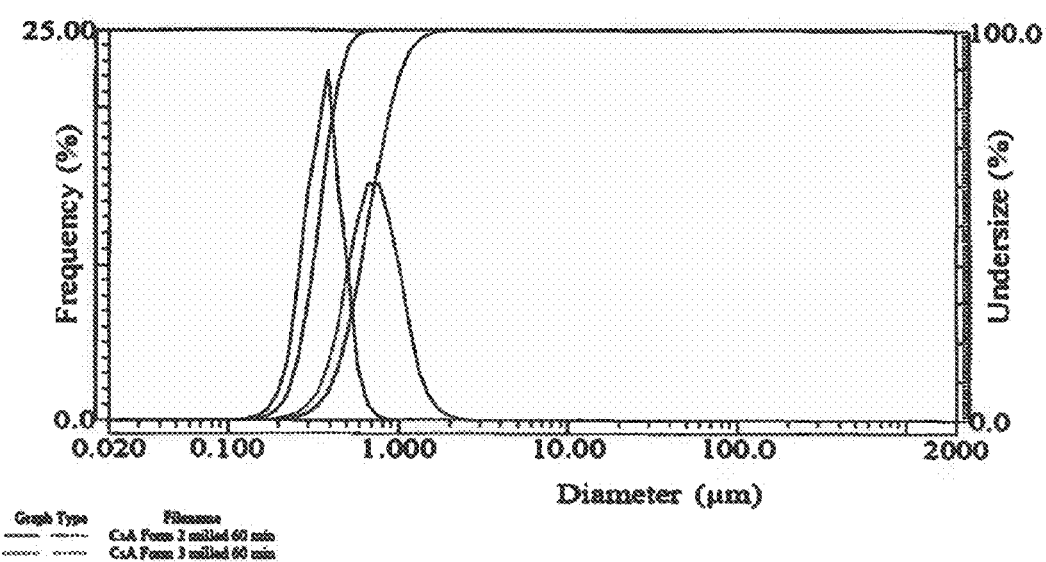
FIG. 4 shows average particle size of a nanosuspension using cyclosporin A Form 3 compared to a nanosuspensions using Form 2 after milling using a microfluidizer. Form 2 Forms a nanosuspension (particle size <1 μm) while Form 3 does not.
Figure 5:
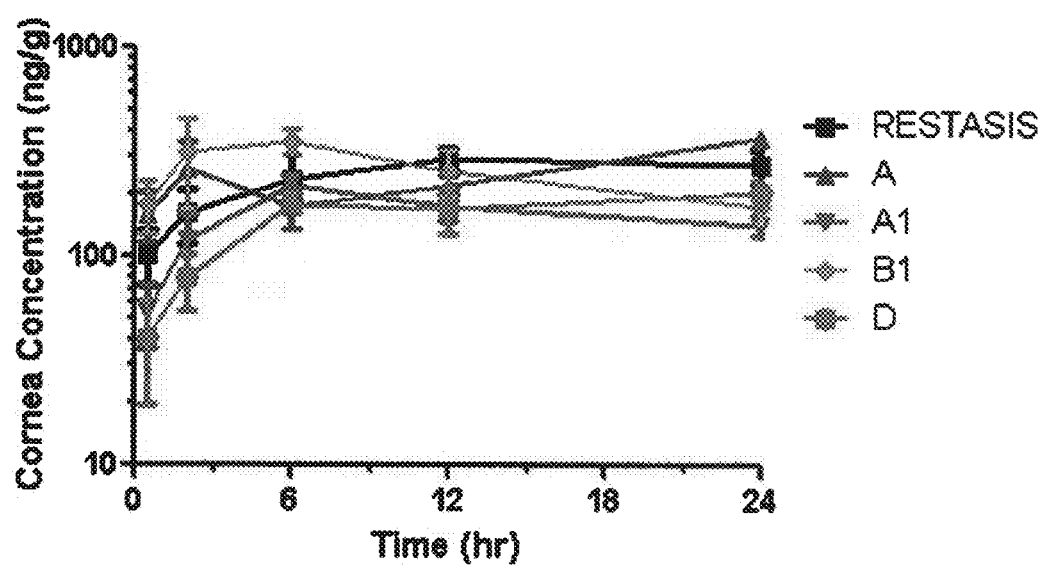
Figure 7:
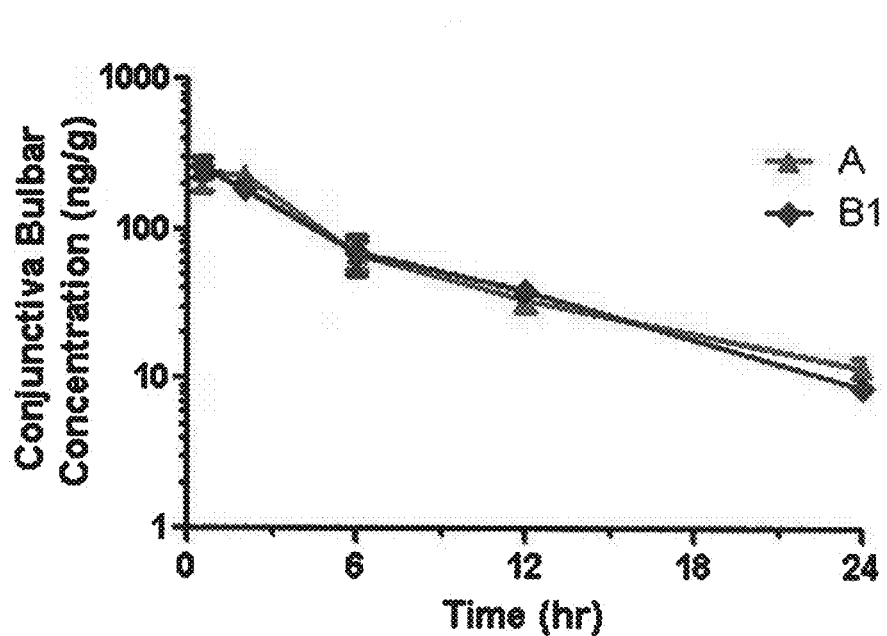

Average particle size of cyclosporin A Form 3 are shown in FIG. 4. Cyclosporin A Form 2 Forms a nanosuspensions (particle size <1 μm) while Form 3 does not.

These experiments show that Form 2 consistently produced nanosuspensions with lower particle size than any other crystalline form of CsA. The smaller particle size of Form 2 nanosuspensions is an advantage over other forms; among other reasons, it is expected to show higher bioavailability due to larger surface area for dissolution and longer retention in the eye, as well as improved physical stability.

Example 2

The inventors prepared the cyclosporin A nanosuspensions listed in Table 2, below:

TABLE 2

Formulations of cyclosporin A prepared in Example 2

| | Ingredient | Restasis ® | A | A1 | B1 | D |
|---|---|---|---|---|---|---|
| | | Concentration (% w/w) | | | | |
| Nano- | CsA | — | 0.05 | 0.05 | 0.01 | 0.05 |
| suspen- | Polysorbate 80 | — | 0.005 | 0.005 | 0.001 | — |
| sion | Na glychocholate | — | — | — | — | from suspension |
| Oil Phase | CsA | 0.05 | — | — | — | — |
| | Castor oil | 1.25 | — | — | — | — |
| Aque- | PS80 | 1 | 0.045 | 0.045 | 0.049 | 0.05 |
| ous | Glycerin | 2.2 | 2.2 | 2.2 | 2.2 | 2.2 |
| Vehicle | Citric acid*H2O | — | — | 0.007 | — | — |
| | Na2HPO4*7H2O | — | — | 0.134 | — | — |
| | Pemulen TR-2 | 0.05 | 0.05 | — | 0.05 | 0.05 |
| | Gellan Gum | — | — | 0.6 | — | — |
| | Purified water | QS | QS | QS | QS | QS |

The inventors administered the above formulations to NZW female rabbits (two rabbits total, one formulation per eye) in a single topical dose. Results are summarized in FIGS. 5-13. They show that formulation B1 delivers a 5-fold lower dose of cyclosporin A (0.01% versus 0.05%) but maintains comparable cornea exposure to 0.05% Restasis® as well as improves delivery to the bulbar and palpebral conjunctiva.

What is claimed is:

1. A method of treating a condition selected from dry eye, blepharitis, meibomian gland disease, impaired corneal sensitivity, allergic conjunctivitis, atopic keratoconjunctivitis, vernal keratoconjunctivitis, and ptyregia, the method comprising the step of administering to a patient having such a condition a formulation comprising cyclosporin A form 2 and a vehicle, wherein the formulation is substantially free of other crystalline forms of cyclosporin A.

2. The method of claim 1, wherein the vehicle comprises at least one surfactant and at least one stabilizer.

3. The method of claim 1, wherein the cyclosporin A form 2 is at a concentration of about 0.01% (w/v) to about 10% (w/v).

4. The method of claim 2, wherein the vehicle comprises one, two, three, four, five, or six surfactants each selected from the group consisting of polyoxyethylene (20) sorbitan monooleate, polyethylene glycol 660 hydroxystearate, polyoxyethylene (40) stearate, poloxamer 188, polyoxyethylene sorbitan monolaurate, and sodium glycocholate.

5. The method of claim 2, wherein the vehicle comprises one, two, three, four, five, or six surfactants each selected from the group consisting of polyoxyethylene (20) sorbitan monooleate at a concentration of about 0.1% to about 5% (w/v), polyethylene glycol 660 hydroxystearate at a concentration of about 0.1% to about 5% (w/v), polyoxyethylene (40) stearate at a concentration of about 0.1% to about 5% (w/v), poloxamer 188 at a concentration of about 0.1% to about 5% (w/v), polyoxyethylene sorbitan monolaurate at a concentration of about 0.1% to about 5% (w/v), and sodium glycocholate at a concentration of about 0.1% to about 5% (w/v).

6. The method of claim 4, wherein the vehicle comprises one, two, three, or four stabilizers each selected from the group consisting of hydroxypropyl cellulose, hydroxypropylmethyl cellulose, hydroxyethylcellulose, polyvinyl pyrolidone, and carboxymethylcellulose.

7. The method of claim 5, wherein the vehicle comprises one, two, three, or four stabilizers each selected from the group consisting of hydroxypropyl cellulose at a concentration of about 0.1% to about 5% (w/v), hydroxypropylmethyl cellulose at a concentration of about 0.1% to about 5% (w/v), hydroxyethylcellulose at a concentration of about 0.1% to about 5% (w/v), and polyvinyl pyrolidone at a concentration of about 0.1% to about 5% (w/v), and carboxymethylcellulose at a concentration of about 0.1% to about 5% (w/v).

8. The method of claim 7, wherein the vehicle further comprises one, two, three, four, five, six, seven, eight, or nine ingredients selected from glycerin, mannitol, crosslinked copolymers of acrylic acid and C10-C30 alkyl acrylate, sodium citrate dihydrate, potassium chloride, boric acid, sodium borate decahydrate, and water.

9. The method of claim 7, wherein the vehicle further comprises one, two, three, four, five, six, seven, eight, or nine ingredients selected from glycerin at concentration of about 1.0% (w/v) to about 2.2% (w/v), mannitol at concentration of about 0.5% (w/v), crosslinked copolymers of acrylic acid and C10-C30 alkyl acrylate at concentration of about 0.01% (w/v) to about 0.1% (w/v), sodium citrate dihydrate at concentration of about 0.4% (w/v), potassium chloride at concentration of about 0.14% (w/v), boric acid at concentration of about 0.25% (w/v), sodium borate decahydrate at concentration of about 0.41% (w/v), and water.

10. The method of claim 1, wherein the condition is dry eye.

11. A method of treating a condition selected from dry eye, blepharitis, meibomian gland disease, impaired corneal sensitivity, allergic conjunctivitis, atopic keratoconjunctivitis, vernal keratoconjunctivitis, and ptyregia, the method comprising the step of administering to a patient having such a condition a formulation comprising particles of cyclosporin A form 2 and a vehicle, wherein the average size (d90) of the particles is less than about 10 µm, and wherein the formulation is substantially free of other crystalline forms of cyclosporin A.

12. The method of claim 11, wherein the average size of the particles is less than about 1 µm.

13. The method of claim 11, wherein the condition is dry eye.

\* \* \* \* \*

UNITED STATES PATENT AND TRADEMARK OFFICE
CERTIFICATE OF CORRECTION

PATENT NO. : 9,238,002 B2
APPLICATION NO. : 14/325167
DATED : January 19, 2016
INVENTOR(S) : Anuradha V. Gore et al.

Page 1 of 2

It is certified that error appears in the above-identified patent and that said Letters Patent is hereby corrected as shown below:

Specification

In column 2, line 49, delete "Lleucyl" and insert -- L-leucyl --, therefor.

In column 2, line 51, delete "Nmethyl" and insert -- N-methyl --, therefor.

In column 4, line 5, delete "1/[o²" and insert -- 1/[$\sigma^2$ --, therefor.

In column 4, line 6, delete "2Fo²)/3" and insert -- 2Fc²)/3 --, therefor.

In column 4, line 8, delete "$R_{nt}$" and insert -- $R_{int}$ --, therefor.

In column 5, lines 39-40, delete "(Polaxamer" and insert -- (Poloxamer --, therefor.

In column 5, line 66, delete "pyrolidone," and insert -- pyrrolidone, --, therefor.

In column 6, line 9, delete "stablizer." and insert -- stabilizer. --, therefor.

In column 6, line 13, after "about" delete "about".

In column 6, lines 21-22, delete "stablizer." and insert -- stabilizer. --, therefor.

In column 7, line 6, delete "ptyregia," and insert -- pterygium, --, therefor.

In column 7, line 7, delete "keratoconjuntivitis," and insert -- keratoconjunctivitis, --, therefor.

In column 7, line 8, delete "comeal" and insert -- corneal --, therefor.

In column 7, line 60, delete "hyperlasia," and insert -- hyperplasia, --, therefor.

In column 8, line 6, delete "formix" and insert -- fornix --, therefor.

In column 8, line 7, delete "madurosis." and insert -- madarosis. --, therefor.

In column 8, line 14, delete "(HLA.DR" and insert -- (HLA-DR --, therefor.

In column 8, line 59, delete "a" and insert -- A --, therefor.

In column 9, line 2, after "1" insert -- . --.

In column 9, line 13, delete "2," and insert -- 2. --, therefor.

In column 9, line 53, delete "glychocholate" and insert -- glycocholate --, therefor.

Signed and Sealed this
Twenty-first Day of June, 2016

Michelle K. Lee
*Director of the United States Patent and Trademark Office*

Claims

In column 10, line 7, in Claim 1, delete "ptyregia," and insert -- pterygium, --, therefor.

In column 10, lines 38-39, in Claim 6, delete "pyrolidone," and insert -- pyrrolidone, --, therefor.

In column 10, line 46, in Claim 7, delete "pyrolidone" and insert -- pyrrolidone --, therefor.

In column 11, line 4, in Claim 11, delete "ptyregia," and insert -- pterygium, --, therefor.